United States Patent [19]

Veligdan

[11] Patent Number: 4,723,448
[45] Date of Patent: Feb. 9, 1988

[54] METHOD FOR REMOTELY INSPECTING SOLID STRUCTURES FOR DISCONTINUITIES UTILIZING LASER TECHNIQUES

[75] Inventor: James T. Veligdan, Upton, N.Y.
[73] Assignee: Westinghouse Electric Corp., Pittsburgh, Pa.
[21] Appl. No.: 884,827
[22] Filed: Jul. 11, 1986
[51] Int. Cl.$^4$ ............................................. G01N 29/04
[52] U.S. Cl. ..................................................... 73/657
[58] Field of Search .................. 73/657, 655, 582, 800

[56] References Cited
U.S. PATENT DOCUMENTS
4,633,715  1/1987  Monchalin ...................... 73/655 X FOREIGN PATENT DOCUMENTS
35228  3/1980  Japan ........................................ 73/655

*Primary Examiner*—Myracle Jerry W.
*Attorney, Agent, or Firm*—Daniel C. Abeles

[57] ABSTRACT

A method for remotely inspecting solid structures for discontinuities other than surface imperfections is disclosed. The method comprises vibrating a solid structure to be inspected while utilizing a laser radar doppler receiver to generate a doppler shifted heterodyne signal resulting from detecting the vibrational frequency of a portion of the solid structure to be inspected. The doppler shifted signal is monitored while scanning the surface of the solid structure.

6 Claims, 7 Drawing Figures

METHOD FOR REMOTELY INSPECTING SOLID STRUCTURES FOR DISCONTINUITIES UTILIZING LASER TECHNIQUES

BACKGROUND OF THE INVENTION

This invention relates to methods for remote inspection of solid structures such as metals, and, in particular, to a method for remotely inspecting solid structures for discontinuities other than surface imperfections. Within the fields of manufacturing and quality control, there often exists a need to remotely inspect a surface for cracks or other discontinuities. In the past, optical techniques have primarily been of the direct detection type utilizing either visible or infrared light. The technique disclosed in the present invention utilizes heterodyne detection instead of direct optical detection. Direct detection has difficulty distinguishing a true material defect from a superficial imperfection such as rust, scale, or minor scratches. The present invention as hereinafter described has the advantage that it will only detect a true discontinuity in a structure and will not give false indications due to surface defects. Another useful application of the present invention is remote analysis of spot weld integrity sheet metal structures. At a point where the sheet metal is spot welded there will be a local change in vibration frequency due to the presence of the additional mass of the weld.

Optical and infrared heterodyne detection is described in articles such as by D. E. LeLange, "Optical Heterodyne Detection," IEEE Spectrum 5, 77 (1968) and by M. C. Teich, "Infrared Heterodyne Detection," Proc. IEEE 56, 37 (1968). An article by W. Puschert "Optical Detection of Amplitude and Phase of Mechanical Displacements in the Angstrom Range," Optic Communications, Vol. 10, No. 4, 357, April 1974, discusses a method for detecting light from a periodically vibrating surface.

SUMMARY OF THE INVENTION

The present invention provides a method for remotely inspecting solid structures for discontinuities other than surface imperfections. The method generally involves vibrating a solid structure to be inspected. A laser radar doppler receiver means is used to generate a doppler shifted heterodyne signal resulting from detecting the vibrational frequency of a portion of the structure to be inspected with the laser doppler receiver means. The generated doppler shifted heterodyne signal is monitored while scanning the surface of the solid structure to be inspected with the laser doppler receiver means to detect discontinuities in the vibrational frequency of the solid structure. The variations in vibrational frequency are indicative of structural discontinuities of the solid structure other than surface imperfections.

Utilizing the present invention with a particular type of laser radar doppler system comprises directing a laser signal beam of predetermined frequency at an acousto-optic tunable filter means. Oscillating the acousto-optic tunable filter means at a predetermined frequency to produce acoustic waves in the filter means propagating in a predetermined direction with respect to the crystal structure with the acousto-optic tunable filter means splitting the laser signal means into a non-diffracted signal beam and a diffracted beam where the diffracted beam differs in frequency from the non-defracted beam by the frequency of the oscillation of the acousto-optic tunable filter.

Either the diffracted beam or non-diffracted beam is then directed to impinge on a portion of a vibrating target solid structure to be remotely inspected. The portion of the vibrating target solid structure causes a doppler shift of the diffracted beam or non-diffracted beam. The target structure is then positioned such that the target structure reflects the doppler shifted diffracted or non-diffracted beam to impinge on a beam combining means, where the diffracted beam and the non-diffracted beam are redirected by the beam combining means to be parallel with respect to one another and directed to impinge on a focusing means. The parallel beams are then converged through the focusing means to be directed onto an optically sensitive detector and amplifier means to produce a doppler shifted heterodyne signal representative of the difference beat frequency of the converged beams. The resulting doppler shifted heterodyne signal is monitored while varying the relative position of the diffracted beam and the vibrating target structure to scan the surface of the target structure to detect discontinuities in the vibrational frequency of the target structure as it is scanned.

BRIEF DESCRIPTION OF THE DRAWINGS

For a better understanding of the invention, reference may be had to the accompanying drawings in which.

BRIEF DESCRIPTION OF THE PREFERRED EMBODIMENT

The present invention provides a non-destructive method for remotely inspecting solid structures for discontinuities other than surface imperfections. The inspection method of the present invention is based on measuring a small difference in vibrational frequency on opposite sides of a crack or in the area of discontinuity. As stated before, the present method assumes that the structure under inspection is in a randomly vibrating environment or that the structure can be vibrated by external means. The present invention is useful for the remote inspection of spot weld integrity in sheet metal structures. At a point where the sheet metal is spot welded there will be a local change in vibration frequency due to the presence of the additional mass.

Figure 1:
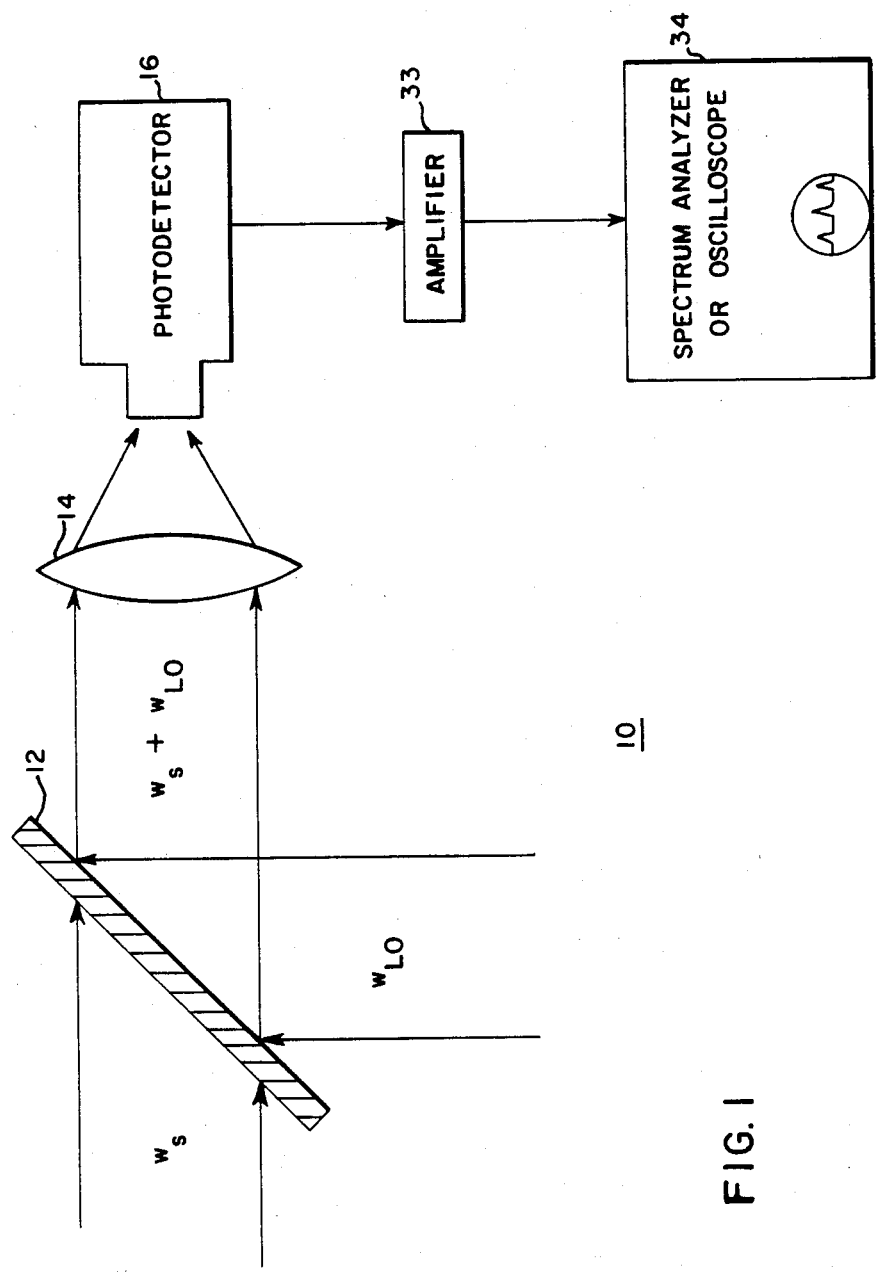
FIG. 1 is a simplified schematic of the laser doppler radar receiver means.

The present invention utilizes a laser doppler radar receiver 10, a simplified schematic of which is shown in FIG. 1. The theory of operation of such a receiver 10 is a signal beam (frequency $\omega_s$) and a local oscillator beam (frequency $\omega_{LO}$) are combined with a beam splitting mirror or in the present case more properly called a beam combiner 12 or other optical device to be parallel and incident on a converging means 14 which converges the two signals $\omega_s$ and $\omega_{LO}$ on a photodetector 16. Assuming that both beams impinge normally on the detector element 16, and both have the same polarization and are fixed in phase, that is coherent with respect to each other, the total electric field amplitude of the detector is $$E_t = E_s \cos(\omega_s t) + E_{LO} \cos(\omega_{LO} t), \quad (1)$$

where $E_s$ and $E_{LO}$ are the amplitudes of the individual waves. Because the physical phenomena which are responsible for the fundamental processes operating in the majority of light detectors require an interaction between incoming photons and electrons, the detector 16 output current is proportional to the light power input. The light power is proportional to the square of the electric field amplitude $|\vec{E}|^2$, so the detector current is related to field amplitude by the relation $$i = \alpha |\vec{E}|^2, \quad (2)$$

These are so called square law detectors.

The signal current i must be proportional to the number of quanta per second incident on the detector, or $P/h\nu$, where P is the incident light power and $h\nu$ the energy of one photon. If N photons are required to generate one electron in the detector, then $\alpha$ must be given by $$\alpha = \frac{e}{h\nu N} = \frac{\eta e}{(h\eta)}, \quad (3)$$

where e is the electron charge and $\eta = 1/N$ the detector quantum efficiency. It can be shown that if the total incident field amplitude were that due to the combined signal and local oscillator signals of the equation (1) above, and assuming $\omega_s$ and $\omega_{LO}$ are close enough together so that the detector can respond to their difference frequency $|\omega_s - \omega_{LO}|$, the response of the detector will be $$i(t) = \alpha \left[ \frac{E_s^2}{2} + \frac{E_{LO}^2}{2} + E_s E_{LO} \cos(\omega_s - \omega_{LO})t \right] \quad (4)$$

$$= i_{DC} + i_{RF}. \quad (5)$$

If the signal and local oscillator amplitudes are coherent but vary by a fixed phase shift:

$$i_{RF} = \alpha E_s E_{LO} \cos[(\omega_s - \omega_{LO})t + \phi] \quad (6)$$

It is the radio frequency portion of the detected current, $i_{RF}$ which can be conveniently amplified, measured and displayed on an oscilloscope, spectrum analyzer or other instrument.

Figure 2:
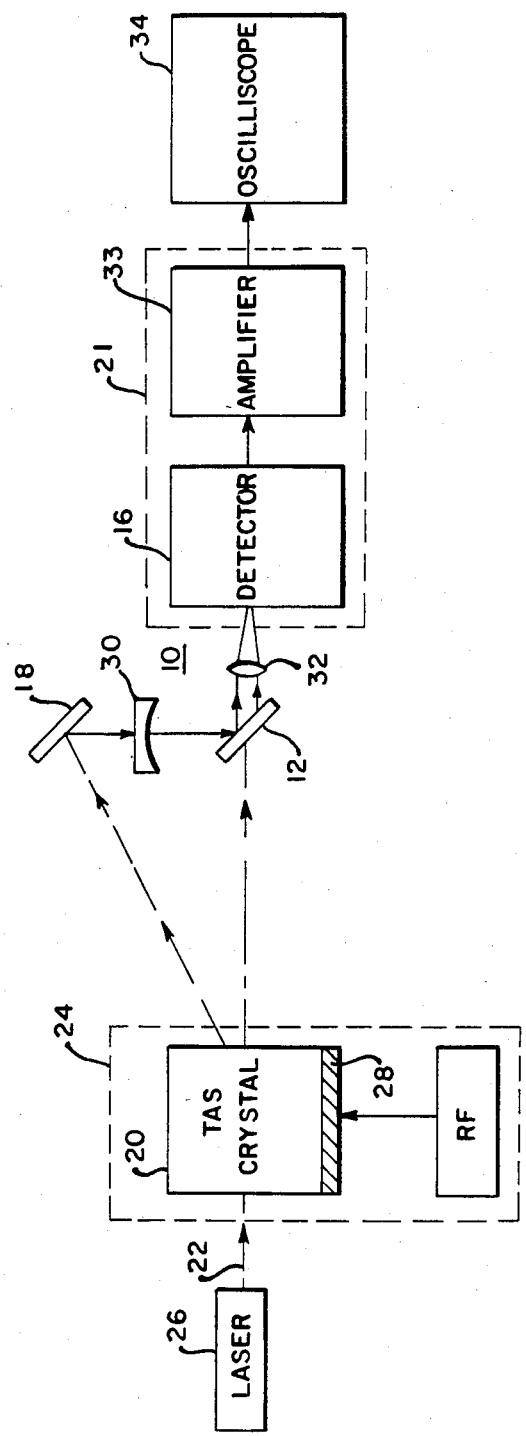
FIG. 2 is a schematic of the laser doppler receiver utilizing an aniostropic Bragg diffractor to provide the necessary frequency offset.

The method of the present invention comprises vibrating a solid target structure 18 as shown in FIG. 2 that is to be inspected. Using a laser radar doppler receiver means 10 generating a doppler shifted heterodyne signal resulting from detecting the vibrational frequency of a portion of the solid structure being inspected with the laser doppler receiver means. Then monitoring the generated doppler shifted heterodyne signal while scanning the surface of the target solid structure 18 to be inspected with the laser doppler receiver 10 to detect discontinuities in the vibrational frequency of the solid structure 18. The variations in vibrational frequency are indicative of the structural discontinuities of the solid structure other than surface imperfections. Surface imperfections will not vary the vibrational frequency of the solid structure.

The preferred embodiment of the present invention comprises directing a laser signal beam of predetermined frequency at an acousto-optic tunable filter means. Oscillating the acousto-optic tunable means at a predetermined frequency to produce acoustic waves in the filter means propagating in a predetermined direction with respect to the crystal structure of the acousto-optic tunable filter means to split the laser signal beam into a non-diffracted signal beam or zero order beam and a diffracted beam where the diffracted beam differs in frequency from the non-diffracted beam by the frequency of oscillation of the acousto-optic tunable filter means. The diffracted beam or non-diffracted beam is then directed to impinge on a portion of a vibrating target structure 18 which is to be remotely inspected. The portion of the vibrating solid structure causes a doppler shift of the diffracted or non-diffracted beam. The target structure is positioned such that the target structure reflects the doppler shifted diffracted or non-diffracted beam to impinge on a beam combining means where the diffracted beam and the non-diffracted beam are redirected by the beam combining means to be parallel with respect to one another and directed to impinge on the focusing means 14. The parallel beams are converged through the focusing means to be directed to an optically sensitive detector and amplifier means 21 to produce a doppler shifted heterodyne signal representative of the difference beat frequency of the converged beams. Monitoring the resulting doppler shifted heterodyne signal while varying the relative position of the diffracted beam of the vibrating target structure to scan the surface of the target structure to detect discontinuities and the vibrational frequency of the target structure as it is scanned. The variations in vibrational frequency are indicative of structural discontinuities of the target structure other than surface imperfections. The present method is useful for evaluating spot welds where a solid structure comprises a sheet metal piece with spot welds to be inspected. The difference in mass of the spot weld compared to other metal being welded will produce a variation in vibrational frequency which may be detected utilizing the method of the present invention.

Figure 3:
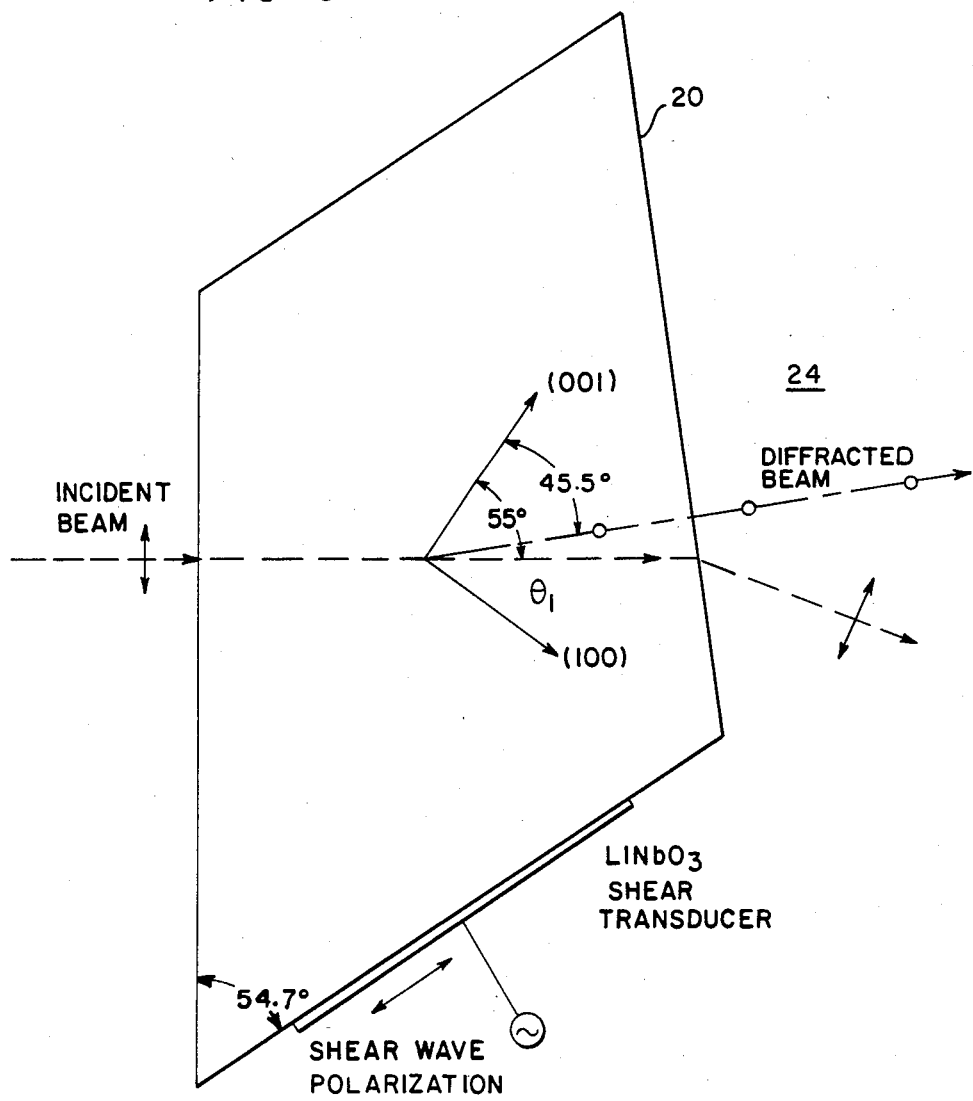
FIG. 3 is a schematic diagram of an aniostropic Bragg diffractor utilizing a thallium arsenide selenide crystal.

In the preferred embodiment as shown in FIG. 2 the method as described preferably utilizes a laser radar receiver utilizing an anisotropic Bragg diffractor 20 such as shown in FIG. 3. Such a diffractor is discussed in detail in a first article by J. D. Feichtner, M. P. Gottlieb and J. J. Conroy, "Tunable Acousto-Optic Filters and Their Applications to Spectroscopy," Proc. SPIE. 82, 106 (1976), and in a second article by the same authors entitled "TlAsSe Noncollinear Acousto-Optic Filter Operation at 10 μm," Appl. Phys. Lett. 34, 1 (1979). In a thallium arsenic selenide anisotropic Bragg diffractor schematically shown in FIG. 3, the interaction between acoustic and light beams not only diffracts the light beam, but also rotates its plane of polarization. This is a so-called "anisotropic Bragg interaction". For a given angle of propagation of the incident "unfocused" light beam of given wavelength $\lambda_o$ with respect to the crystal c-axis (001), the interaction will be carried out very efficiently if the acoustic frequency $f_a$ is chosen to satisfy the "phase matching" condition.

$$f_a = \frac{V_a \Delta \eta}{\lambda^o} (\sin^4 \theta_i + \sin^2 2\theta_i)^{\frac{1}{2}} \qquad (7)$$

Where $\theta_i$ is the angle of propagation of the light beam with respect to the crystal c-axis, and $$\Delta n = |n_e - n_o|$$

is the birefrigerance of the crystal. In equation (7), $$\Delta n \approx 0.18, \ V_a = 1.05 \times 10^5 \text{ cm/sec, and } \theta_i = 30°.$$

At a fixed $\theta_i$, the range of optical wavelengths over which the interaction will take place efficiently is given approximately by $$2\Delta\lambda \simeq \frac{1.8\pi\lambda_o^2}{bL \sin^2 \theta_i} \qquad (8)$$

Here, b is a dispersive constant equal in value to 1.1, and L is the interaction length between light and sound. In the modulator used in this embodiment, the design value is L=2.5 cm (this is the transducer length as utilized).

From the equations (7) and (8) one can calculate the acoustic frequency bandwidth over which effective modulation should be possible, as a function of $\theta_i$ and L, for a fixed wavelength of incident light. The result is, for the full width at half maximum, $$2\Delta f_a = f_a \left(\frac{2\Delta\lambda}{\lambda}\right) (\sin^4\theta_i + \sin^2 2\theta_i)^{\frac{1}{2}} \qquad (9)$$

$$= f_a \left(\frac{1.8\pi\lambda_o}{bL}\right) (1 + 4\cos^2\theta_i)$$

Figure 4:
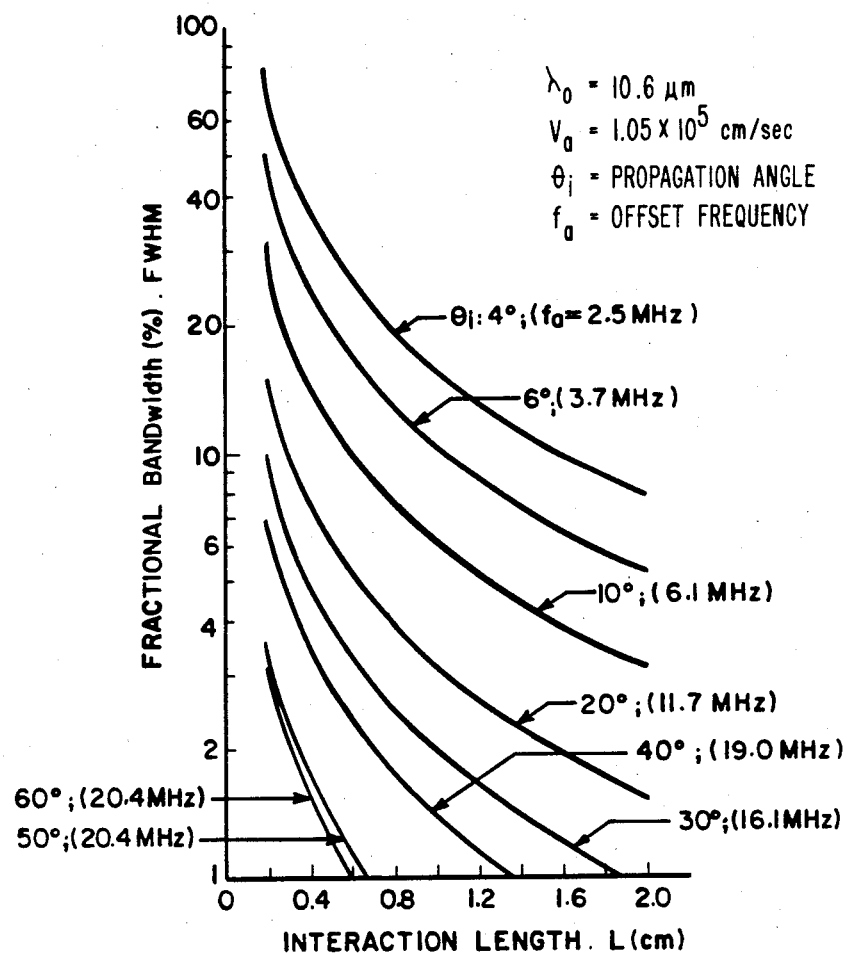
FIG. 4 is a graph of interaction length as a function of fractional bandwidth.

The results are plotted in FIG. 4. It can be seen that for large functional tuning ranges, one must operate at low values of $\theta_i$ and with short interaction lengths, L. The major disadvantage of low $\theta_i$ and short L is that the acoustic power density required for a given diffraction efficiency increases at those $\theta_i$ and L values. Only very small local oscillator powers are needed, however, so the power density requirement is not considered critical. In the preferred embodiment as shown in FIGS. 2 and 3, the modulator operated at $\theta_i = 30°$ and the interaction length L was designed to 2.5 cm. From FIG. 4 it can be seen that this indicates a fractional tuning bandwidth of less than 1% at the 16.1 MHz acoustic frequency. The actual calculated value is 0.79%, or 127 kHz.

The observed $\Delta f_a$ (FWM) is about 500 MHz and the usable bandwidth (for detectable heterodyne signals) is of the order of 1.5 MHz. The method of the preferred embodiment of the present invention as shown in FIGS. 2 and 3 comprises directing a laser signal beam 22 of predetermined frequency at an acousto-optic tunable filter means 24. The laser signal beam is generated by a laser means 26 which may be, for example, an Apollo Model 570 line tunable $CO_2$ laser and is used as the source of signal frequency radiation at 10.6 μm. Other lasers at any wavelength may of course be used. Because of the characteristics of the Apollo Model 570, the laser was passively stabilized by using invar optical cavity construction, and is line tunable by means of a grating. The output is polarized in the vertical direction. The frequency stability claimed by the manufacturer is one part in $10^9$ (short term), (~30 kHz) and a refrigerated closed cycle cooler is necessary for stable operation. Although for the present invention, only about 100 milliwatts laser power is needed for the preferred embodiment, it was found necessary to operate the Apollo 570 laser at approximately 15 watts to obtain the required stability. The laser energy for the experiment was taken from a reflection of a NaCl beam splitter (not shown) and for optical table experiments, 95% of the energy is dumped onto a firebrick. The beam was then apertured to 3 mm to eliminate the gaussian wings, it is directed into the thalium arsenic selenide acousto-optic optical tunable filter 24 as shown in FIG. 2. The acousto-optic tunable filter 24 is used in the non-collinear configuration with the incident light entering the crystal at an angle of 30° with respect to the optic axis. For this particular angle, the acousto-optic tunable filter transducer drive frequency must be approximately 16 MHz to diffract the 10.6 μm light.

The transducer of the acousto-optic tunable filter 28 was driven by a Wavetek-Rockland Model 560 frequency synthesizer followed by an AR Model 10LA RF amplifier. The transducer 28 is operated in the CW mode with approximately 0.5 watts of power as measured on the power meter of the RF amplifier. The zero order beam $\omega_S$ and the diffracted beam $\omega_{LO}$ exit the acoustic-optical tunable filter with an angular separation of 10.75 degrees and with a polarization of the diffracted beam $\omega_{LO}$ rotated 90°. In order to observe the heterodyne signal with these two beams, it is first necessary to make polarizations of each beam the same and then make the two beams collinear to minimize the wavefront angular mismatch at the detector for optimum photo mixing at the detector, the angular alignment of the two wavefronts should be maintained to within $\lambda/a$ where a is the detector aperture.

To satisfy the polarization criterion in this embodiment a ZnSe half waveplate 30 is inserted in the diffracted beam $\omega_{LO}$ before it is mixed via the beam combiner 12 with the zero order beam $\omega_S$. A lens 32 such as a 10 centimeter F1 lens is used to focus the two beams on the HgCdTe detector 16. The photoconductive detector is peaked for 10.6 μm and is operated 77° K. The heterodyne signal is then fed into a monitor means 34 such as a Techtronics 1121 preamplifier with a voltage gain of 50 which also serves as a low pass filter to eliminate high frequency noise. The heterodyne signal is finally displayed on a Hewlett-Packard 8553 spectrum analyzer. The power density of the 10.6 μm beam in the modulator is about 5 W/cm$^2$.

Figure 5:
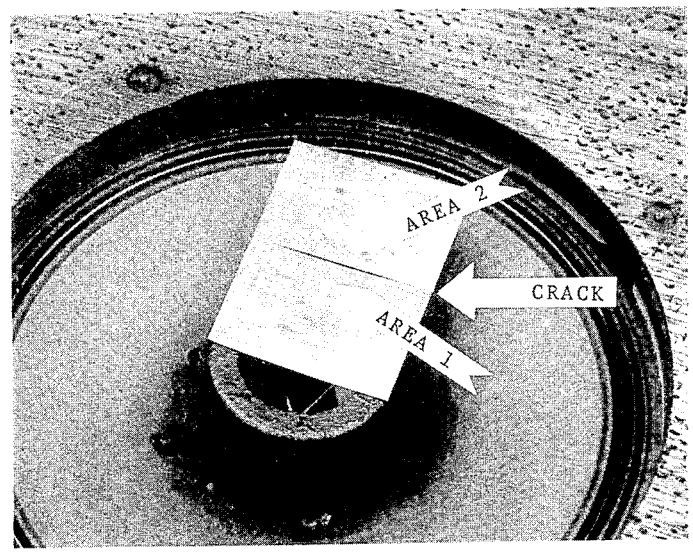
FIG. 5 is a schematic diagram representative of a piece of sheet metal which has been cut to simulate a crack.
Figure 6A:
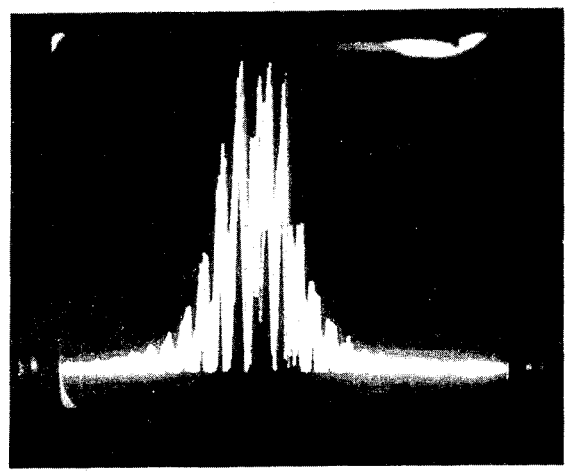
FIG. 6A is a photograph of the heterodyne signal originating from the side of the crack marked "area 1"
Figure 6B:
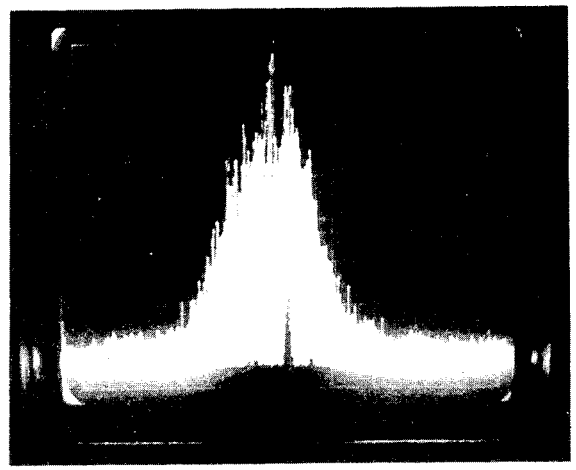
FIG. 6B is a photograph of the heterodyne signal originating from the side of the crack marked "area 2".

Referring to FIGS. 5, 6A, 6B, FIG. 5 represents a piece of sheet metal which has been partially cut through to simulate a crack which is vibrated by means of a loud speaker. The heterodyne signal originating from the side of the crack marked "area 1" is shown in FIG. 6A. The FIG. in 6B shows the heterodyne signal originating from the other side of the crack marked "area 2". The obvious difference that is observed in these two figures, FIGS. 6A, 6B represents the difference in the vibrational frequency spectrum on opposite sides of the crack.

I claim:

1. A method for remotely inspecting solid structures for discontinuities other than surface imperfections, said method comprising:

(a) vibrating a solid structure to be inspected;

(b) generating, using a laser radar doppler receiver means, a doppler shifted heterodyne signal resulting from detecting the vibrational frequency of a portion of said solid structure to be inspected with said laser doppler receiver means;

(c) monitoring said generated doppler shifted heterodyne signal while scanning the surface of said solid structure to be inspected with said laser doppler receiver means to detect variations in vibrational frequencies of said solid structure, said variations in vibrational frequency indicative of structural discontinuities of said solid structure other than surface imperfections.

2. The method of claim 1, wherein said solid structure comprises a sheet metal piece with a spot weld to be inspected.

3. A method for remotely inspecting solid structures for discontinuities other than surface imperfections, said method comprising:

(a) directing a laser signal beam of predetermined frequency at an acousto-optic tunable filter means;

(b) oscillating said acousto-optic tunable filter means at a predetermined frequency to produce acoustic waves in said filter means propagating in a predetermined direction with respect to the crystal structure of the acousto-optic tunable filter means to split said laser signal beam into a non-diffracted signal beam and a diffracted beam where said diffracted beam differs in frequency from said non-diffracted beam by the frequency of said oscillation of said acousto-optic tunable filter means;

(c) directing said diffracted beam to impinge on a portion of a vibrating target solid structure to be remotely inspected, said portion of said vibrating target solid structure causing a doppler shift of said diffracted beam;

(d) positioning said target structure such that said target structure reflects said doppler shifted diffracted beam to impinge on a beam combining means, where said diffracted beam and said non-diffracted beam are redirected by said beam combining means to be parallel with respect to one another and directed to impinge on a focusing means;

(e) converging said parallel beams through said focusing means to be directed to an optically sensitive detector and amplifier means to produce a doppler shifted heterodyne signal representative of the difference beat frequency of the converged beams; and (f) monitoring said resulting doppler shifted heterodyne signal while varying the relative position of said diffracted beam and said vibrating target structure to scan the surface of said target structure to detect discontinuities in the vibrational frequency of the target structure as it is scanned, said variations in vibrational frequency indicative of structural discontinuities of said target structure other than surface imperfections.

4. The method of claim 3, wherein said solid structure comprises a sheet metal piece with a spot weld to be inspected.

5. A method for remotely inspecting solid structures for discontinuities other than surface imperfections, said method comprising:

(a) directing a laser signal beam of predetermined frequency at an acousto-optic tunable filter means;

(b) oscillating said acousto-optic tunable filter means at a predetermined frequency to produce acoustic waves in said filter means propagating in a predetermined direction with respect to the crystal structure of the acousto-optic tunable filter means to split said laser signal beam into a non-diffracted signal beam and a diffracted beam where said diffracted beam differs in frequency from said non-diffracted beam by the frequency of said oscillation of said acousto-optic tunable filter means;

(c) directing said non-diffracted beam to impinge on a portion of a vibrating target solid structure to be remotely inspected, said portion of said vibrating target solid structure causing a doppler shift of said non-diffracted beam;

(d) positioning said target structure such that said target structure reflects said doppler shifted non-diffracted beam to impinge on a beam combining means, where said diffracted beam and said non-diffracted beam are redirected by said beam combining means to be parallel with respect to one another and directed to impinge on a focusing means;

(e) converging said parallel beams through said focusing means to be directed to an optically sensitive detector and amplifier means to produce a doppler shifted heterodyne signal representative of the difference beat frequency of the converged beams; and (f) monitoring said resulting doppler shifted heterodyne signal while varying the relative position of said diffracted beam and said vibrating target structure to scan the surface of said target structure to detect discontinuities in the vibrational frequency of the target structure as it is scanned, said variations in vibrational frequency indicative of structural discontinuities of said target structure other than surface imperfections.

6. The method of claim 5, wherein said solid structure comprises a sheet metal piece with a spot weld to be inspected.

* * * * *